US010792385B2

(12) United States Patent
Kreiner et al.

(10) Patent No.: US 10,792,385 B2
(45) Date of Patent: Oct. 6, 2020

(54) STERILIZING FLOOR ARRAY

(71) Applicant: AT&T Intellectual Property I, L.P., Atlanta, GA (US)

(72) Inventors: Barrett M. Kreiner, Woodstock, GA (US); Ryan Schaub, Peachtree Corners, GA (US); Timothy Knezevich, Mentor, OH (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 0 days.

(21) Appl. No.: 16/364,092

(22) Filed: Mar. 25, 2019

(65) Prior Publication Data
US 2019/0216964 A1 Jul. 18, 2019

Related U.S. Application Data

(63) Continuation of application No. 15/670,922, filed on Aug. 7, 2017, now Pat. No. 10,238,763.

(51) Int. Cl.
*A61L 2/10* (2006.01)
*A61L 2/24* (2006.01)
*B66B 31/02* (2006.01)

(52) U.S. Cl.
CPC .................... *A61L 2/24* (2013.01); *A61L 2/10* (2013.01); *A61L 2202/11* (2013.01); *A61L 2202/14* (2013.01); *A61L 2202/25* (2013.01); *B66B 31/02* (2013.01)

(58) Field of Classification Search
CPC . A61L 2/10; A61L 2/24; A61L 2/0047; A61L 2202/14; A61L 2202/20
See application file for complete search history.

(56) References Cited

U.S. PATENT DOCUMENTS

| 6,216,918 | B1 | 4/2001 | Saveliev et al. |
| 6,382,467 | B2 | 5/2002 | Saveliev et al. |
| 7,372,044 | B2 | 5/2008 | Ross |
| 8,058,629 | B2 | 11/2011 | Long |
| 8,277,741 | B2 | 10/2012 | McCabe |
| 8,337,770 | B2 | 12/2012 | Wind |
| 8,512,631 | B2 | 8/2013 | Kerr |

(Continued)

FOREIGN PATENT DOCUMENTS

| CN | 205285164 U | 6/2016 |
| FR | 3019744 A1 | 10/2015 |

(Continued)

*Primary Examiner* — Wyatt A Stoffa

(57) ABSTRACT

Various devices for sterilizing a surface and an object in contact with the surface are disclosed. For example, a first device includes an ultraviolet light source, a touch sensor, a processing system, and a computer-readable medium. The computer-readable medium stores instructions which, when executed by the processing system, cause the processing system to perform operations that include detecting, via the touch sensor, a tactile state of the device, detecting a tactile state of at least one additional device, determining, based upon the tactile states, that the device is on an edge of a pattern of contact between an object and a surface comprising the device and the at least one additional device, and implementing an action associated with the ultraviolet light source in response to determining that the device is on the edge of the pattern of contact.

20 Claims, 6 Drawing Sheets

(56) References Cited

U.S. PATENT DOCUMENTS

| | | | |
|---|---|---|---|
| 8,617,464 B2 | 12/2013 | Kerr | |
| 8,784,731 B2 | 7/2014 | Gil et al. | |
| 8,973,197 B2 | 3/2015 | Omidi | |
| 9,211,352 B2* | 12/2015 | Kassel | A61L 2/10 |
| 9,463,258 B2 | 10/2016 | Kassel et al. | |
| 9,579,410 B2* | 2/2017 | Simmons | A61L 2/10 |
| 9,764,050 B1* | 9/2017 | Almeida | A61L 2/10 |
| 10,117,958 B2* | 11/2018 | Dombrowsky | A61L 2/0047 |
| 2005/0025662 A1* | 2/2005 | Lestician | A23L 3/28 |
| | | | 422/24 |
| 2006/0192100 A1 | 8/2006 | Zubarev et al. | |
| 2008/0310996 A1* | 12/2008 | Kim | A61L 9/20 |
| | | | 422/24 |
| 2009/0123331 A1 | 5/2009 | Ross | |
| 2010/0104470 A1* | 4/2010 | McCabe | A61L 2/10 |
| | | | 422/22 |
| 2010/0193709 A1 | 8/2010 | Dalton | |
| 2011/0286882 A1 | 11/2011 | Wu | |
| 2011/0291995 A1 | 12/2011 | Shr et al. | |
| 2012/0187313 A1* | 7/2012 | Clark | A61L 2/10 |
| | | | 250/492.1 |
| 2013/0154441 A1 | 6/2013 | Redmond | |
| 2013/0187775 A1 | 7/2013 | Marsden et al. | |
| 2015/0133259 A1 | 5/2015 | Nakamura et al. | |
| 2015/0238645 A1 | 8/2015 | Agafonov et al. | |
| 2015/0290346 A1* | 10/2015 | Kassel | A47L 23/02 |
| | | | 422/186.12 |
| 2016/0000951 A1 | 1/2016 | Kreiner et al. | |
| 2016/0089461 A1* | 3/2016 | Kassel | A61L 2/202 |
| | | | 250/453.11 |
| 2016/0175896 A1* | 6/2016 | Montgomery | A47L 23/00 |
| | | | 250/454.11 |
| 2016/0372311 A1 | 12/2016 | Takahashi et al. | |
| 2017/0290937 A1* | 10/2017 | Dobrinsky | A43B 17/10 |
| 2018/0055959 A1* | 3/2018 | Lin | A61L 9/20 |
| 2018/0071414 A1* | 3/2018 | Dujowich | A61L 2/10 |
| 2018/0153367 A1* | 6/2018 | Dombrowsky | E04F 15/02405 |
| 2018/0154032 A1* | 6/2018 | Dombrowsky | A61L 2/24 |

FOREIGN PATENT DOCUMENTS

| | | |
|---|---|---|
| JP | 1052480 A | 2/1998 |
| WO | 2016162581 A1 | 10/2016 |

\* cited by examiner

STERILIZING FLOOR ARRAY

This application is a continuation of U.S. patent application Ser. No. 15/670,922, filed Aug. 7, 2017, now U.S. Pat. No. 10,238,763, which is herein incorporated by reference in its entirety.

The present disclosure relates to devices, apparatuses, and methods for sterilizing a surface and an object in contact with the surface. For example, the present disclosure provides for the intelligent use of ultraviolet light on surfaces, e.g., floors, steps, stoops, escalators, or similar surfaces to decontaminate and sterilize both the surface and objects that come into contact with the surface.

BRIEF DESCRIPTION OF THE DRAWINGS

The teachings of the present disclosure can be readily understood by considering the following detailed description in conjunction with the accompanying drawings, in which.

To facilitate understanding, identical reference numerals have been used, where possible, to designate identical elements that are common to the Figures.

DETAILED DESCRIPTION

Figure 1:
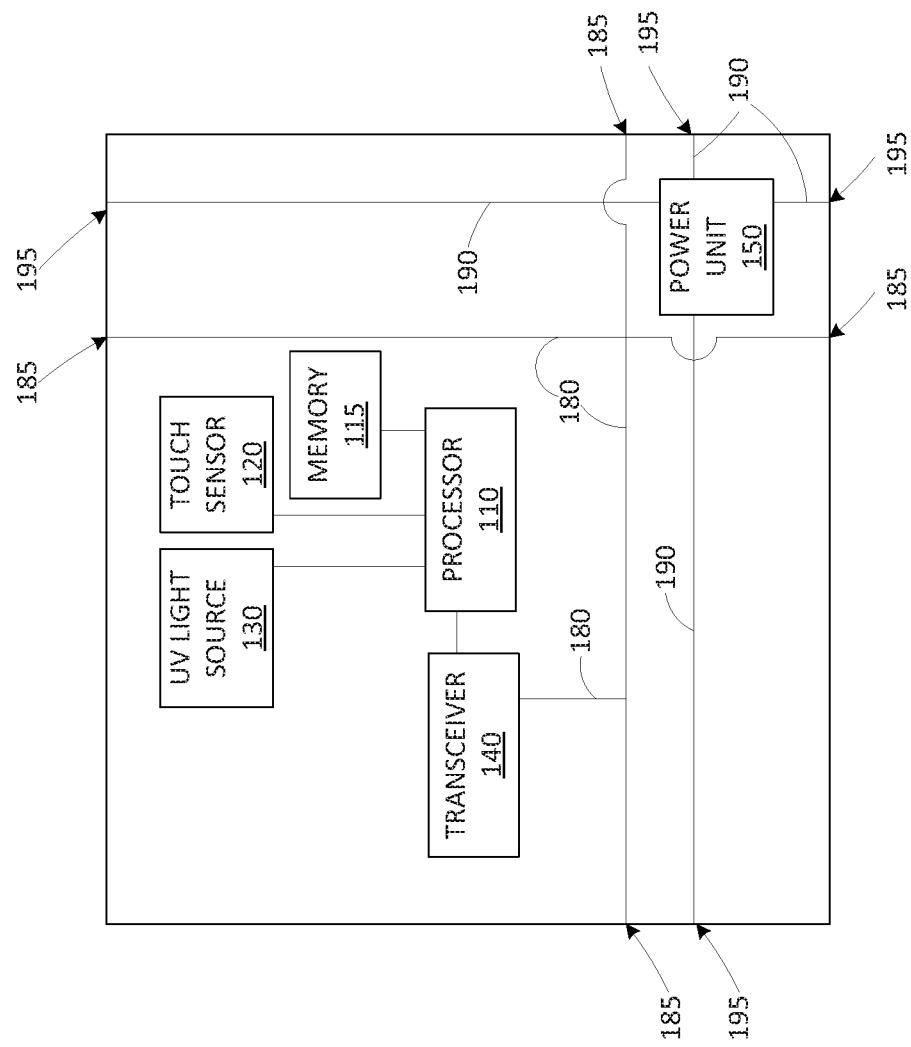
FIG. 1 illustrates an example device, or tile, according to one embodiment of the present disclosure.

Pathogens, comprising bacteria, protozoa and viruses that are infectious agents that cause diseases in humans, are a significant health hazard. The systemic over-use of antibiotics in the treatment of human diseases, as well as in livestock management, has created a situation where many previously treatable strains of bacteria are now resistant to many antibiotics. Additionally, there are limited sterilization treatments for viruses and environmental protozoa that do not themselves have significantly negative health impact on people. It has been recognized that the broad spectrum ultraviolet (UV) light, commonly found in sunlight, is effective in sterilization, preventing a pathogen from infecting a host, because UV light penetrates the pathogens' smaller cells, or virus virions, and damages the DNA of the pathogen, effectively killing it directly or preventing it from reproducing.

The present disclosure describes devices, apparatuses, computer-readable media, and methods for sterilizing a surface. In one example, a device includes an ultraviolet light source, a touch sensor, a processing system, and a computer-readable medium. The computer-readable medium stores instructions which, when executed by the processing system, cause the processing system to perform operations. The operations include detecting, via the touch sensor, a tactile state of the device, detecting a tactile state of at least one additional device, determining, based upon the tactile state of the device and the tactile state of the at least one additional device, that the device is on an edge of a pattern of contact between an object and a surface comprising the device and the at least one additional device, and implementing an action associated with the ultraviolet light source in response to determining that the device is on the edge of the pattern of contact.

In another example, an additional apparatus, computer-readable medium, and method are disclosed. For example, a method includes a processing system receiving signals from a plurality of touch sensors of a plurality of devices forming a surface, and detecting, based upon the signals from the plurality of touch sensors, a pattern of contact between an object and a surface comprising the plurality of devices. In one example, the plurality of devices further includes a plurality of ultraviolet light sources. The processing system may then send instructions to the plurality of devices to provide an ultraviolet light emitting pattern via the plurality of ultraviolet light sources, where the ultraviolet light emitting pattern is based upon the pattern of contact.

In another example, an additional device, computer-readable medium, and method are disclosed. For example, a device includes an ultraviolet light source, a touch sensor, a processing system, and a computer-readable medium. The computer-readable medium stores instructions which, when executed by the processing system, cause the processor to perform operations. The operations include detecting, via the touch sensor, a tactile state of the device, reporting the tactile state of the device to a controller, receiving an instruction from the controller for operating the ultraviolet light source, and implementing an action associated with the ultraviolet light source in response to the instruction.

Shoes, wheels, human feet, animal paws or hoofs, and similar items are in regular ground contact and in proximity to biological microbial contamination (bacteria, virus, mold, fungi, and similar) on the ground. These items are regularly contaminated and cross multiple physically distinct domains with different implicit or explicit levels of cleanliness or contamination, including indoors, outdoors, residential, commercial, and vehicles, which allows biological (and other) contaminants to inadvertently cross from one domain to another. Some domains, such as cars, trains, planes, buses, elevators, escalators, and travellators are themselves mobile, increasing the cross contamination risk by relocating the contaminated surfaces themselves. Ground contact surface contamination mitigation is normally considered only in high risk areas, and cross contamination (tracking) is common but rarely considered, thereby resulting in significant disease spread.

Examples of the present disclosure comprise an ultraviolet (UV) light sterilization system in a tile/grid surface arrangement. In one example, each tile includes a touch sensor and a UV light source. The touch sensors may comprise pressure sensors such that when pressure is applied to specific areas of the surface (e.g., comprising multiple tiles), UV light is emitted from below at the point(s) of contact to sterilize both where the surface is contacted and the portion of the object that is making the contact. The UV light source may comprise a UV light emitting diode (LED).

In one example, only the area that is contacted is UV exposed, reducing inadvertent exposure to other parts of the body or object, avoiding distracting lighting effects, and reducing the overall power needs of the implementation. In one example, the pressure exerted upon the surface provides some or all of the power utilized to emit the UV light (e.g., via a UV LED). For instance, the pressure sensors may comprise piezoelectric or fluid motion capture units, or the tiles may include separate piezoelectric or fluid motion capture units to generate power from compression. In another example, tiles/devices may be powered via embedded solar collector(s) or may be externally powered. In one example, power may be shared via power connections from tile to tile. Some or all of the tiles may also include rechargeable batteries.

In one example, external wired/wireless communications can control additional functionality. For instance, all UV light sources on a surface may be remotely activated when a room is empty. The implementation can be in a tile, a mat, or the like, and may be embedded in a flooring or comprise an overlay to an existing or underlying flooring. Examples of the present disclosure may also be implemented as flexible units for applications such as escalators, travellators, conveyor belts in a warehouse or factory, and so forth.

In one example, UV illumination may be most intense for maximum sterilization of transient contacts, and applied at a continued lower intensity level for extended contact. In one example, tiles may coordinate with each other, or via a centralized controller, to determine the edges of an object, such as a footprint. The tiles on the edges of the footprint may then use a lesser intensity of UV light or may not activate in order to provide a guard band and prevent UV light from spilling over. In another example, extra UV activation may be provided in tiles that are not contacted, but which are near/adjacent to the tiles that are contacted. For example, a person's pants may hang over the shoe and drag on the floor, thus becoming contaminated, but not providing enough pressure to activate a touch sensor of a tile. Therefore, UV activation may be expanded beyond the tiles that are actually contacted by a footstep or other object. In one example, a lesser intensity UV may be used on tiles outside of the actual footprint (e.g., to avoid unnecessary skin exposure). In another example, higher intensity may be used, to give a better chance of decontamination on the irregularly shaped surfaces of the pants.

In this regard, it should be noted that examples of the present disclosure may utilize UV light of any one or more of UV-A, UV-B, and UV-C bands. However, example devices may employ at least one light-emitting diode (LED) or other UV light sources emitting in the UV-C range, e.g., within a portion of the spectrum from 190-225 nanometers, that disrupts reproduction of smaller pathogens, e.g., viruses, bacteria and protozoa, but is non-damaging to larger human cells. More specifically, light at approximately 207 nanometers (e.g., at or around 207 nanometers), is able to penetrate the smaller bacteria and protozoa cells, as well as virions (virus particles) but does not penetrate larger human cells.

In one example, the system may select which UV band(s) to activate at various tiles depending upon the type of contact and/or the object making the contact. For example, a paw or bare foot may be restricted to application of UV-C, whereas for a box, UV-A, UV-B, or both UV-A and UV-B (and also UV-C) may be applied, and so on. In one example, for a shoe contact, UV-A, UV-B, and/or UV-C may be applied at tiles near the center of the shoe print, while around the edges, application may be restricted to UV-C. In one example, the "edge" may comprise the last tiles that are contacted within a contact pattern of the object. In another example, the "edge" may comprise tiles that are just beyond the last tiles contacted by the object. In general, different UV bands, intensities, and application durations can be utilized depending upon whether contact is a human footstep versus an animal contact, whether a footstep is barefoot or with a shoe, the pressure of a footstep and/or a stride size (e.g., adult versus child, running versus walking, etc.), whether the contact is a box, a cart wheel, or other inanimate objects instead of a live object, depending upon the level of protection desired (e.g., surgical suites, emergency rooms, ambulances, etc. versus homes, offices, hotels, and so forth), depending upon the power available, depending upon power utilization preferences as determined by a manufacturer, installer, owner, operator, and so on.

In one example, one or more tiles may including central processing units (CPUs), microcontrollers, or the like, e.g., a processor and memory/computer-readable media to perform operations to collectively distinguish between different types of contacting objects based upon multiple touch sensors, to distinguish the edges of objects, and so forth, as well as to select the different UV bands, intensities, and application durations to be applied via various tiles (e.g., higher intensity in the center of footprint, lesser intensity at the edges, only UV-C at edge tiles, and so on). The processor may perform pattern matching to match a pattern of contact of an object with a surface to a library of known patterns. In one example, a particular person may be tracked through a system to determine that the person's shoes have been completely sterilized. Therefore, the intensity of UV illumination for this person may be scaled down thereafter. However, if the person is approaching a surgical suite, the person's shoes may be subjected to higher intensity UV, regardless of whether the shoes have already been well sterilized. In another example, a pattern of footsteps may be tracked and the intensity of UV light applied at each successive step may be reduced. For instance, upon an initial contact with a surface, it may be determined that a pair of shoes is contacting the surface (as compared to any other kind of object). Thereafter, the same pair of shoes may be identified as making subsequent contact with other parts of the surface based upon a contact pattern of the same size and shape, e.g., the same shoe size and sole pattern.

In one example, the calculations and operations described above may be performed by one or more computing units integrated in one or more of the tiles, which may provide instructions to various tiles to collectively irradiate a footprint or other contacts in a controlled manner (e.g., decreasing intensity near the edge, UV-C near the edge or over the edge, and so forth). In another example, an external computing device, e.g., a "controller," may receive touch sensor information from various tiles, perform various calculations, and return instructions to one or more tiles in the grid with regard to whether or not to apply UV light, which band(s) of UV light to apply, the duration and/or intensity of the light to apply, and so on.

In one example, tiles may include wireless communication modules. In another example, tiles may modularly plug into one another to create shared buses via which tiles can communicate with one another and/or with an external computing device, and which may also be used to receive external power and/or to distribute power among the respective tiles (for both power that may be externally provided or for power that is generated by any one or more of the interconnected tiles using internal solar cells, piezoelectric transducers, or other types of internal power generators). These and other features of the present disclosure are described in greater detail below and in connection with FIGS. 1-6.

To aid in understanding the present disclosure, FIG. 1 illustrates in greater detail an example device, or tile 100, according to the present disclosure. As illustrated in FIG. 1, the tile 100 includes a UV light source 130 and a touch sensor 120. In one example, the UV light source 130 comprises a UV LED, which may provide a negligible (or zero) contribution to the overall thickness of the tile 100. However, examples of the present disclosure may also utilize incandescent or halogen UV light bulbs. The touch sensor 120 may comprise a piezoelectric touch sensor, e.g., a piezoelectric transducer, or a fluid motion capture unit, e.g., employing reverse electro-wetting, or reverse electro-wetting with a bubbler, a resistive touch sensor, a surface capacitive sensor, a projected capacitive sensor, a surface acoustic wave (SAW) sensor, an infrared sensor, and so forth. In one example, the thickness of the tile 100 may account for the thickness of the touch sensor 120, inclusive of electrode films, substrate layers, protective layers, spacer layers, reflective tape layers, and so forth, depending upon the particular type of touch sensing technology utilized for touch sensor 120.

Figure 6:
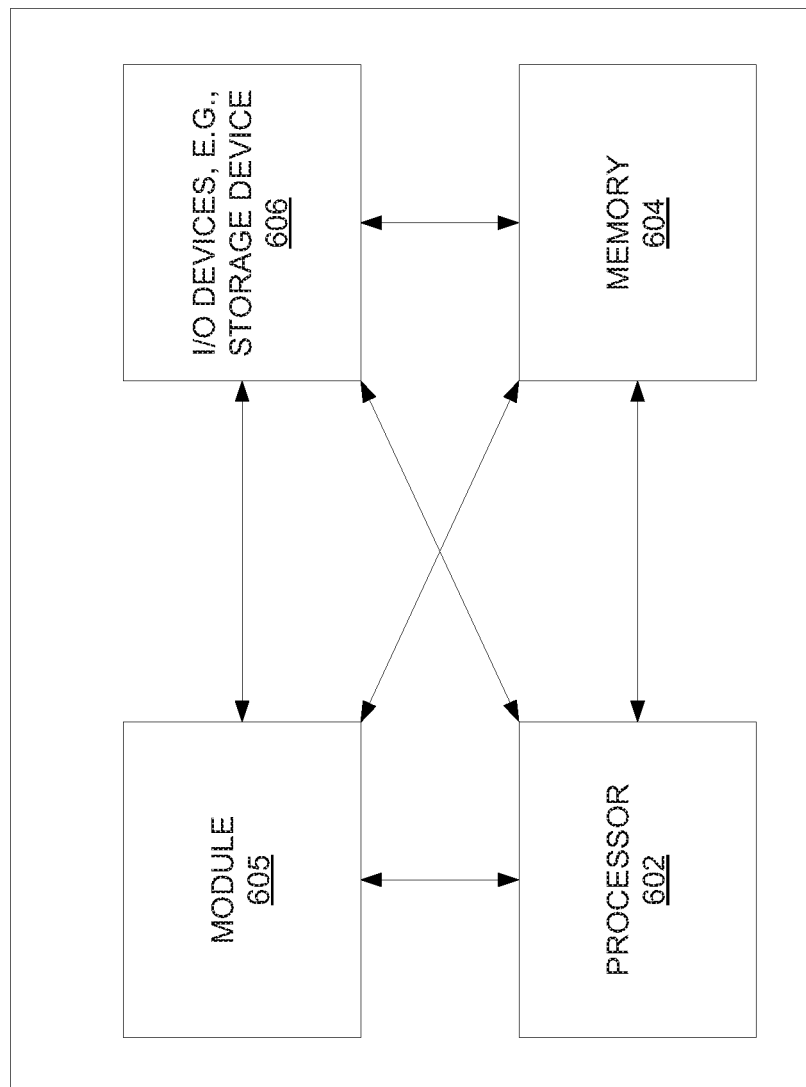
FIG. 6 illustrates an example high-level block diagram of a computer specifically programmed to perform the steps, functions, blocks, and/or operations described herein.

In the example of FIG. 1, the tile 100 further includes a processor 110 configured to perform various operations in connection with sterilizing a surface and an object in contact with the surface. The processor 110 is connected to the touch sensor 120 to receive signals indicating a contact of an object with the tile 100. The processor 110 is also connected to the UV light source 130 to provide signals to activate and/or to disengage emission of UV light from the UV light source 130. In one example, memory 115 may store instructions which, when executed by processor 110, cause the processor to perform various operations as described in the example method 300, method 400, and/or method 500 below. In one example, processor 110, and/or processor 110 together with memory 115 may comprise a central processing unit (CPU), a microcontroller, or the like. In addition, it should be noted that as used herein, the terms "configure," and "reconfigure" may refer to programming or loading a processing system with computer-readable/computer-executable instructions, code, and/or programs, e.g., in a distributed or non-distributed memory, which when executed by a processor, or processors, of the processing system within a same device or within distributed devices, may cause the processing system to perform various functions. Such terms may also encompass providing variables, data values, tables, objects, or other data structures or the like which may cause a processing system executing computer-readable instructions, code, and/or programs to function differently depending upon the values of the variables or other data structures that are provided. As referred to herein a "processing system" may comprise a computing device including one or more processors, or cores (e.g., as illustrated in FIG. 6 and discussed below) or multiple computing devices collectively configured to perform various steps, functions, and/or operations in accordance with the present disclosure.

As illustrated in FIG. 1, the tile 100 also includes a transceiver 140 for communicating with other tiles and/or with a centralized controller via a communication bus 180. In the example of FIG. 1, transceiver 140 is for wired communications. However, in another example, transceiver 140 may be for wireless communications, e.g., for Institute for Electrical and Electronics Engineers (IEEE) 802.11 based communications (e.g., "Wi-Fi"), IEEE 802.15 based communications (e.g., "Bluetooth", "ZigBee", etc.), and so forth. The transceiver 140 may send and receive communications as part of a wired or wireless ad-hoc and/or mesh network of other tiles (and in some examples, including a controller).

In the example of FIG. 1, tile 100 further includes a power unit 150 for generating, distributing, storing, and/or receiving electrical power. For instance, power unit 150 may comprise a rechargeable battery that may provide power to components of the tile 100 and may further provide power to or receive power from other tiles via power distribution lines 190 and power ports 195. In one example, power unit 150 may alternatively or additionally comprise a piezoelectric transducer, a fluid motion capture unit, and so forth. In another example, the touch sensor 120 may comprise a piezoelectric transducer or a fluid motion capture unit to both convert pressure/mechanical energy into electrical energy and to detect an object touching the tile 100. In such an example, touch sensor 120 may distribute electrical energy to power unit 150 for distribution to other components of tile 100 and/or to additional interconnected tiles. Alternatively, or in addition, touch sensor 120 may distribute at least a portion of the electrical energy that is generated directly to other components of tile 100. In another example, power unit 150 may comprise a solar cell to generate and store solar energy, and to distribute electrical power. In still another example, power unit 150 may comprise a solar cell as well as a piezoelectric transducer or a fluid motion capture unit, or may comprise a solar cell and receive additional electrical power from a touch sensor 120 comprising a piezoelectric transducer or a fluid motion capture unit. For ease of illustration, connections between power unit 150 and other components of tile 100 are omitted from the example of FIG. 1.

The communication bus 180 may be externally connected to a controller and/or to other tiles via communication ports 185. Similarly, the power distribution lines 190 may be connected to a power source and/or to other tiles via power ports 195. For instance, additional tiles may have the same or similar dimensions and layout as tile 100 such that the additional tiles may be connected via the communication ports 185 and/or power ports 195 on any side of tile 100. In addition, if the tile 100 is placed at the edge of a surface, a controller may be connected to tile 100 via one of the communication ports 185 on a side of tile 100 that is exposed at the edge of the surface. The controller may communicate with the tile 100 and may also communicate with additional connected tiles via the communication bus 180. Similarly, a power source may be connected to the tile 100 via one of the power ports 195 on the side of the tile 100 that is exposed at the edge of the surface. Power received from a power source may then be further distributed to other connected tiles via power distribution lines 195. These aspects of the present disclosure are further illustrated in connection with the example of FIG. 2.

In one example, all or a portion of the components of tile 100 may comprise an integrated circuit, or may comprise components that are attached to an integrated circuit that may be situated between at least a top external layer and a bottom external layer of the tile 100. The top external layer (and any other layers above the UV light source 130) may be fully or partially transparent to allow UV light to irradiate any object that comes into contact with the tile 100. It should also be noted that although FIG. 1 illustrates a tile 100 with a UV light source 130, a touch sensor 120, a power unit 150, and so forth, in other, further, and different examples, a tile may include multiple touch sensors, UV light sources, power units, etc. In addition, although tile 100 is illustrated as having a rectangular shape, in other, further, and different examples, a tile may have another shape, such as triangular tiles, hexagonal tiles, irregular shaped tiles, and so forth.

Figure 2:
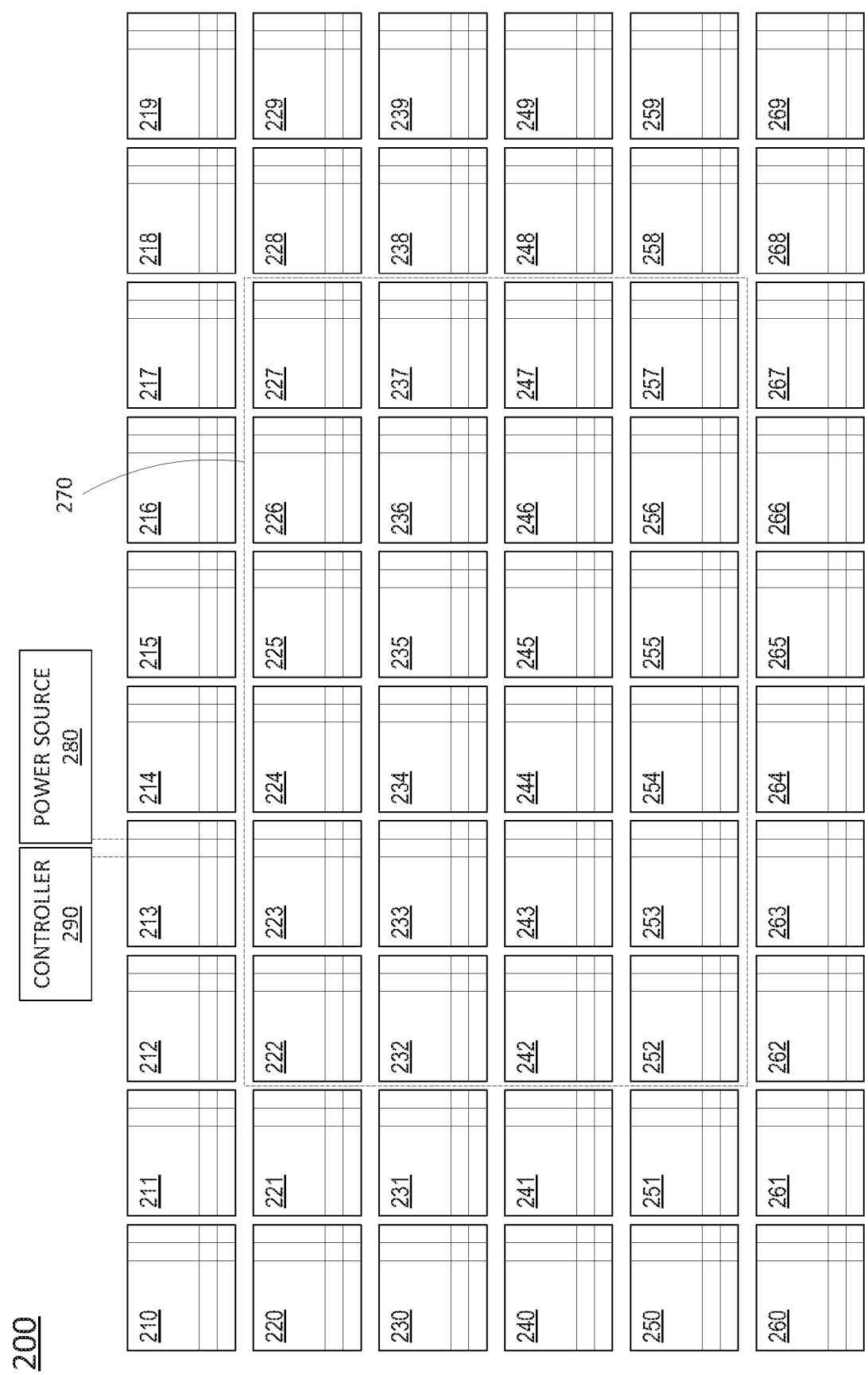
FIG. 2 illustrates an example system, according to one embodiment of the present disclosure.

To aid in understanding the present disclosure, FIG. 2 illustrates an example system 200, according to the present disclosure. As illustrated in FIG. 2, system 200 includes interconnected tiles 210-269 arranged in a grid. For ease of illustration, tiles 210-269 are illustrated with a gap between adjacent tiles. However, it should be understood that tiles 210-269 may be physically interconnected, in addition to having electrical interconnections for signaling and communications, and/or for power distribution. For instance, tiles 210-269 may have the same or a similar form as the example tile 100 of FIG. 1. Collectively, the tiles 210-269 may comprise a "surface." The tiles 210-269 may be deployed as a floor and/or a floor covering. For instance, the tiles 210-269 may be deployed over a concrete slab or over a wood sub-floor, may be deployed over hardwood floor or carpeting, and so forth. Tiles 210-269 may also be deployed over outdoor surfaces, such as wood decking, stone and masonry patios, steps, stoops, and so forth. In one example, each of the tiles 210-269 may include a pattern for interlocking with adjacent tiles to form the surface.

As further illustrated in FIG. 2, the system 200 may include an external controller 290 and a power source 280. The controller 290 and power source 280 are illustrated as connecting to the grid of tiles 210-269 via tile 213, e.g., via a communication port and a power port respectively. Accordingly, the controller 290 may communicate with any of the tiles 210-269 via communication buses of the tiles 210-269. Similarly, power source 280 may provide power to tiles 210-269 via power distribution lines of the tiles 210-269. For ease of illustration, details of the communication buses, power distribution lines, and other components of the tiles 210-269 are omitted from FIG. 2. However, it should be understood that tiles 210-269 may respectively include all or a portion of the components of the example tile 100 of FIG. 1. In one example, the controller 290 and tiles 210-269 may communicate as a wired or wireless mesh and/or ad-hoc network.

In one example, the power source 280 may comprise an alternating current (AC) power source, e.g., a connection to a wall outlet, or a hardwired connection to a junction box, a circuit breaker, a main electrical panel, a sub-panel, and so forth. In one example, the power source 280 may comprise one or more of: a rechargeable battery, a generator, a solar cell, a solar panel and/or a solar array, a wind turbine, and so forth. The controller 290 may comprise a computing system, such as computing system 600 depicted in FIG. 6, and may be configured to provide one or more functions for sterilizing a surface and an object in contact with the surface, in accordance with the present disclosure.

To illustrate, controller 290 may receive signals from tiles 210-269 indicating when the respective tiles have been contacted by an object. Alternatively, or additionally, the controller 290 may receive signals from tiles 210-269 indicating that the respective tiles are not being contacted by an object. In one example, tiles 210-269 may utilize any contention scheme to coordinate the sending of signals to the controller 290. Continuing with the present example, tiles 223-227, 232-237, 242-247, and 252-257 may send signals indicating that the respective tiles have been contacted. From these signals, and with knowledge of the layout of the tiles 210-269, the controller 290 may determine that the signals indicate a pattern of contact 270 of an object with the portion of the surface comprising tiles 223-227, 232-237, 242-247, and 252-257. In one example, the controller 290 may determine a type of object based upon a shape of the pattern of contact 270, a size of the pattern of contact 270, the strengths of the signals indicating how hard the respective tiles have been contacted, and so forth. For instance, the controller 290 may distinguish between human footsteps, animal contacts, and/or inanimate objects, whether a footstep is barefoot or with a shoe, whether a contact is an adult versus a child or a person running versus walking, e.g., based upon pressure/force, and timing measurements from touch sensors of the respective tiles 223-227, 232-237, 242-247, and 252-257, in conjunction with the size and shape of the pattern of contact 270, and so forth.

In one example, the controller 290 may include a library of patterns of known objects, or may have access to an external data source storing such a library. The controller 290 may therefore compare the pattern of contact 270 to one or more patterns of known objects to determine what has contacted the portion of the surface comprising tiles 223-227, 232-237, 242-247, and 252-257. Depending upon a determination of the type of object making the contact (e.g., a human, animal, or inanimate object), the size of the object (e.g., an adult versus a child), whether a contact is a bare foot or a type of footwear (for human footsteps), and so forth, the controller 290 may then select a UV light emitting pattern, in accordance with the present disclosure. In particular, the controller 290 may execute instructions which direct different UV light emitting patterns to be applied depending upon criteria such as: the size and shape of the pattern of contact 270, the type of object detected, level of disinfection/sterilization desired (e.g., surgical suites, emergency rooms, ambulances, etc. compared homes, offices, hotels, etc.), depending upon the power available, depending upon power utilization preferences as determined by a manufacturer, installer, owner, operator, and so forth. The UV light emitting patterns may include combinations of the UV band(s) of UV light, the intensities, and the application durations to be applied via various tiles.

As just one example, the controller 290 may detect that the contact is an inanimate object, such as wheels on a rolling cart, the leg of a chair or table, and so forth. In one example, to protect the eyes and other parts of a human that may be moving the object, the controller 290 may select a UV light emitting pattern that restricts the emission of UV light around the edges of the pattern of contact 270. For instance, a lesser intensity or no application of UV light may be applied at tiles 222-227, 232, 237, 241, 247, and 252-257, or an application of only UV-C light may be applied at these tiles as compared to a higher intensity and/or an application of UV-A and/or UV-B light at tiles in the interior of the pattern of contact 270 (e.g., at tiles 233-236 and 243-246). In another example, a lesser intensity of UV light or only UV-C light may be applied at tiles 211-218, 221, 228, 231, 238, 241, 248, 251, 258, and 261-268. In this regard, it should be noted that depending upon the particular configuration, e.g., based on a manufacturer, owner, operator, or facility preference, that the "edge" of the pattern of contact 270 may comprise the outer tiles that are contacted within the pattern of contact 270, or tiles adjacent to and just beyond the outer tiles that are contacted within the pattern of contact 270.

It should be noted that the system 200 is illustrative of one architecture that is suitable for implementing examples of the present disclosure. Thus, the present disclosure may also include any other different tile layouts, grid configurations, and mixtures of components in various tiles that are suitable for implementing examples of the present disclosure for sterilizing a surface and an object in contact with the surface. Thus, those skilled in the art will realize that the system 200 may be expanded to include additional tiles, power sources, controllers, and so forth, or modifying or substituting those illustrated in FIG. 2, without altering the scope of the present disclosure. As an example, the controller 290 may be deployed at a location that is different from the location of tiles 210-269. For instance, controller 290 may be deployed in a different room within a same facility, or may be maintained "in the cloud," i.e., reachable via the Internet in general.

In another example, operations that are described as being performed by controller 290 may instead be performed by a processor within one or more of tiles 210-269. In another example, different tiles may have different processing capabilities, different types of UV LEDs that may be available, different types of touch sensors, different power generation and/or power storage capabilities, and so forth. Thus, for instance, not all of the tiles may be capable of or configured to perform the operations of controller 290, but may still be configured to communicate touch signals and to receive UV light activation signals.

In addition, the foregoing examples of the patterns of contact that may be detected, and the UV light emitting patterns that may be applied are described for illustrative purposes only. For instance, in other examples, a higher intensity of UV light may be applied at tiles beyond the pattern of contact 270. For instance, a manufacturer, owner, operator, or facility may prefer to provide enhanced UV light sterilization for loose clothing, portions of furniture near the surface, but which do not make contact with the surface, and so on. In still another example, the processor 290 may track a pattern of contact that includes multiple footsteps, and may apply diminishing intensities of UV light for each successive footstep, e.g., footsteps further down a monitored path will receive a decreasing amount of UV light and so on.

In still another example, tiles 210-269 may operate in a decentralized manner (e.g., without an external controller and without one or more of tiles 210-269 operating as a controller). For instance, each of tiles 210-269 may be configured to communicate with adjacent (connected) tiles to determine whether the tile is on the edge of a pattern of contact and to select whether or not to activate a UV light source depending upon whether it is determined that the tile is on the edge. For example, tile 254 may send a signal to tiles 244, 253, 255, and 264 indicating that tile 254 is being contacted by an object. Tile 254 may also receive signals from any of these adjacent tiles that are also being contacted. For example, tile 254 may receive signals from tiles 244, 253, and 255 indicating that each of these tiles is also being contacted. However, no signal (or a signal indicating no contact, e.g., a "non-contact" state) may be received from tile 264.

Accordingly, the processor of tile 254 may determine that it is at an edge of the pattern of contact 270 when: tile 254's own touch sensor indicates contact of an object, tiles 244, 253, and 255 provide signals indicating that each of these tiles is also being contacted, but tile 265 is not being contacted. In such an example, tile 254 may be configured to either suppress activation of a UV light source, to reduce an intensity and/or a duration of application of a UV light, e.g., as compared to if the tile 254 determines that it is a tile within the interior of a pattern of contact (such as, tile 244, for instance), to activate only a UV-C light source or a UV-C portion of a light source, and so forth. In a similar manner, tile 241, for example, may determine that it is at the edge of the pattern of contact 270 (e.g., just outside the tiles that are actually contacted). If the system 200 is configured to apply UV light at or beyond the edge of the pattern of contact of an object, then tile 241 may also determine that it should activate a UV light source, even though tile 241 does not itself detect that it is contacted by the object. Thus, these and other modifications are all contemplated within the scope of the present disclosure.

Figure 3:
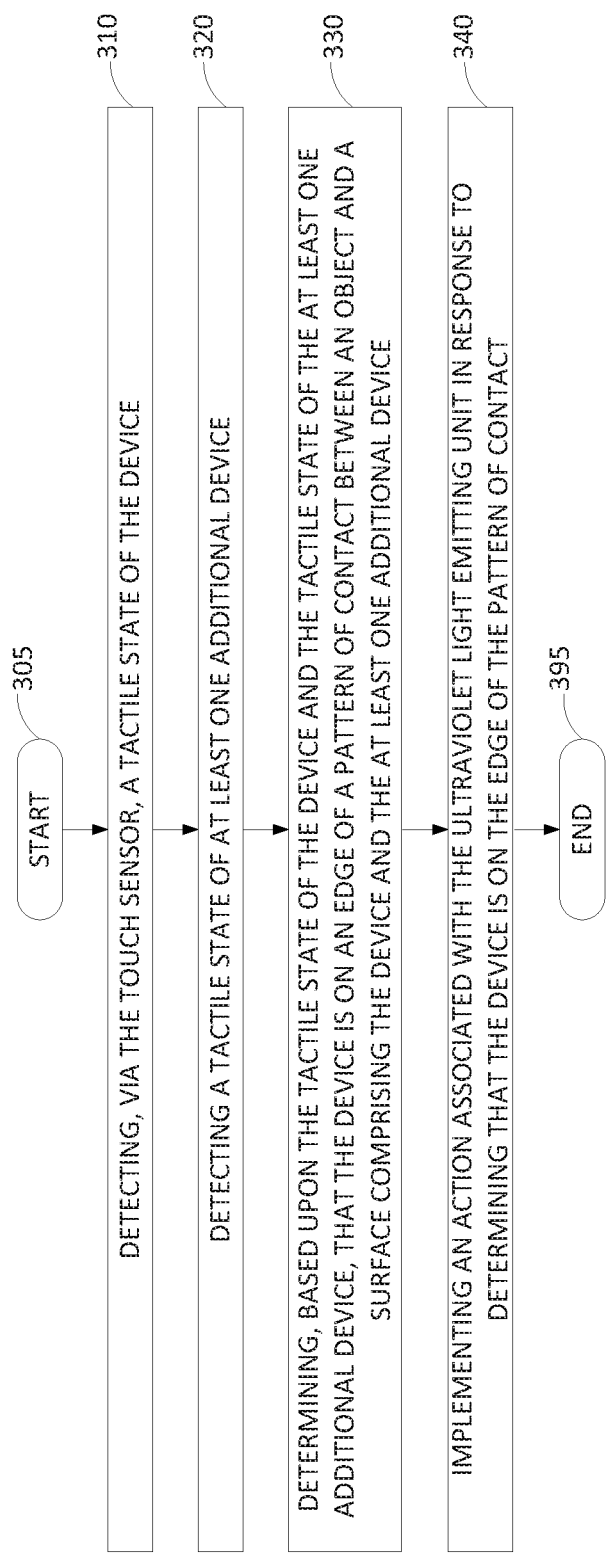
FIG. 3 illustrates a flowchart of an example method for sterilizing a surface and an object in contact with the surface, according to one embodiment of the present disclosure.

FIG. 3 illustrates a flowchart of an example method 300 for sterilizing a surface and an object in contact with the surface. In one embodiment, the method 300 is performed by a device such as tile 100 of FIG. 1, or any of tiles 210-269 of FIG. 2. Alternatively, or in addition, the steps, functions, or operations of method 300 may be performed by a device or system 600, and/or processor 602 as described in connection with FIG. 6 below. For instance, the system 600 may represent a tile 100 of FIG. 1, or any of tiles 210-269 of FIG. 2. For illustrative purposes, the method 300 is described in greater detail below in connection with an example performed by a processor, such as processor 602. The method begins in step 305 and proceeds to step 310.

At step 310, the processor detects, via a touch sensor, a tactile state of a device, or tile, in which the processor is deployed. For instance, the tactile state may comprise a "contact" state where the touch sensor detects contact by an object and a "non-contact" state where no contact by an object is detected by the touch sensor. In one example, the "contact" state may be further refined by an indication of the pressure or amount of force of the contact. The touch sensor may comprise a piezoelectric touch sensor, e.g., a piezoelectric transducer, or a fluid motion capture unit, e.g., employing reverse electro-wetting, or reverse electro-wetting with a bubbler, a resistive touch sensor, a surface capacitive sensor, a projected capacitive sensor, a surface acoustic wave (SAW) sensor, an infrared sensor, and so forth. In an example where the touch sensor comprises a resistive touch sensor, a surface capacitive sensor, a projected capacitive sensor, a surface acoustic wave (SAW) sensor, or an infrared sensor, the device may further include a power source comprising at least one of a piezoelectric transducer, a fluid motion capture unit, or a solar cell.

At step 320, the processor detects a tactile state of at least one additional device. For example, the device and the at least one additional device may comprise all or a portion of a surface. In one example, the device and the at least one additional device may be adjacent devices, e.g., tiles, within the surface. In one example, the device includes a pattern for interlocking with a plurality of additional devices/tiles to form the surface. The surface may comprise, for example, a floor, an escalator, a travellator, a conveyor belt, and so forth. The at least one additional device may have a same or similar configuration as the device, e.g., having at least a touch sensor and a UV light source. The tactile state of the at least one additional device may be detected by receiving a signal from the at least one additional device that indicates the at least one additional device is being contacted and/or a signal indicating that the at least one additional device is not being contacted. In one example the signal from the at least one additional device may also indicate a pressure or amount of force of a contact. In one example, the signal from the at least one additional device may be received via a transceiver of the device. The signal may be sent and received via wired or wireless communication and may utilize ad hoc and/or mesh networking protocols.

At step 330, the processor determines, based upon the tactile state of the device and the tactile state of the at least one additional device, that the device is on an edge of a pattern of contact between an object and a surface comprising the device and the at least one additional device. For instance, the device and the at least one additional device may be interconnected with one another as adjacent devices, or may be nearby to one another, e.g., within one or two positions. In one example, the device and the at least one additional device may further be deployed in a grid with further devices (e.g., further tiles). In one example, the processor may determine that the device is on the edge of the pattern of contact when the tactile state of the device is a "contact" state, and the tactile state of the at least one additional device is "non-contact" state. For instance, the device may be a last device within a pattern of contact moving away from a center of the pattern of contact that includes a number of devices. The processor may also determine that the device is on the edge of the pattern of contact when the tactile state of the device is "non-contact" state and the tactile state of the at least one additional device is a "contact" state. For instance, the device may be just beyond a last device within a pattern of contact moving away from a center of the pattern of contact.

At step 340, the processor implements an action associated with a UV light source in response to determining that the device is on the edge of the pattern of contact. For instance, when the tactile state of the device is a contact state and the tactile state of the at least one additional device is a non-contact state, the action may comprise reducing an intensity of the UV light source, e.g., as compared to devices within an interior of the pattern of contact, or suppressing an activation of the UV light source, e.g., where it is typical to activate the UV light source in response to a "contact" state of the touch sensor, unless the device is on the edge of the pattern of contact. In another example, when the tactile state of the device is a contact state and the tactile state of the at least one additional device is a non-contact state, the action may comprise activating only a UV-C band portion of the UV light source. For instance, the UV light source may include UV emitters in a plurality of UV wavelength bands.

In another example, when the tactile state of the device is a non-contact state and the tactile state of the at least one additional device is a contact state, the action may comprise activating the UV light source. For instance, the activating the UV light source may comprise activating only a UV-C portion of the UV light source. In general, the UV light source may be activated, or an activation of the UV light source may be suppressed, the duration of the application of the UV light source may be longer or shorter, the intensity may be higher or lower, the particular UV band(s) that is/are activated may be adjusted, and so forth depending upon the particular implementation. For example, some implementations may call for devices/tiles on the edges of a pattern of contact to use a lesser intensity of UV light or to not activate in order to provide a guard band and prevent UV light from spilling over. In another example, extra UV activation may be provided in devices/tiles that are not contacted, but which are near/adjacent to the devices/tiles that are contacted. Therefore, UV activation may be expanded beyond the devices/tiles that are actually contacted by a footstep or other object. In one example, a lesser intensity UV may be used on tiles outside of the actual pattern of contact (e.g., to avoid skin exposure). In another example, a higher intensity may be used, to give a better chance of decontamination on the irregularly shaped surfaces of a person's pants, shoelaces, or other hanging clothing. Following step 340, the method 300 proceeds to step 395 where the method ends.

Figure 4:
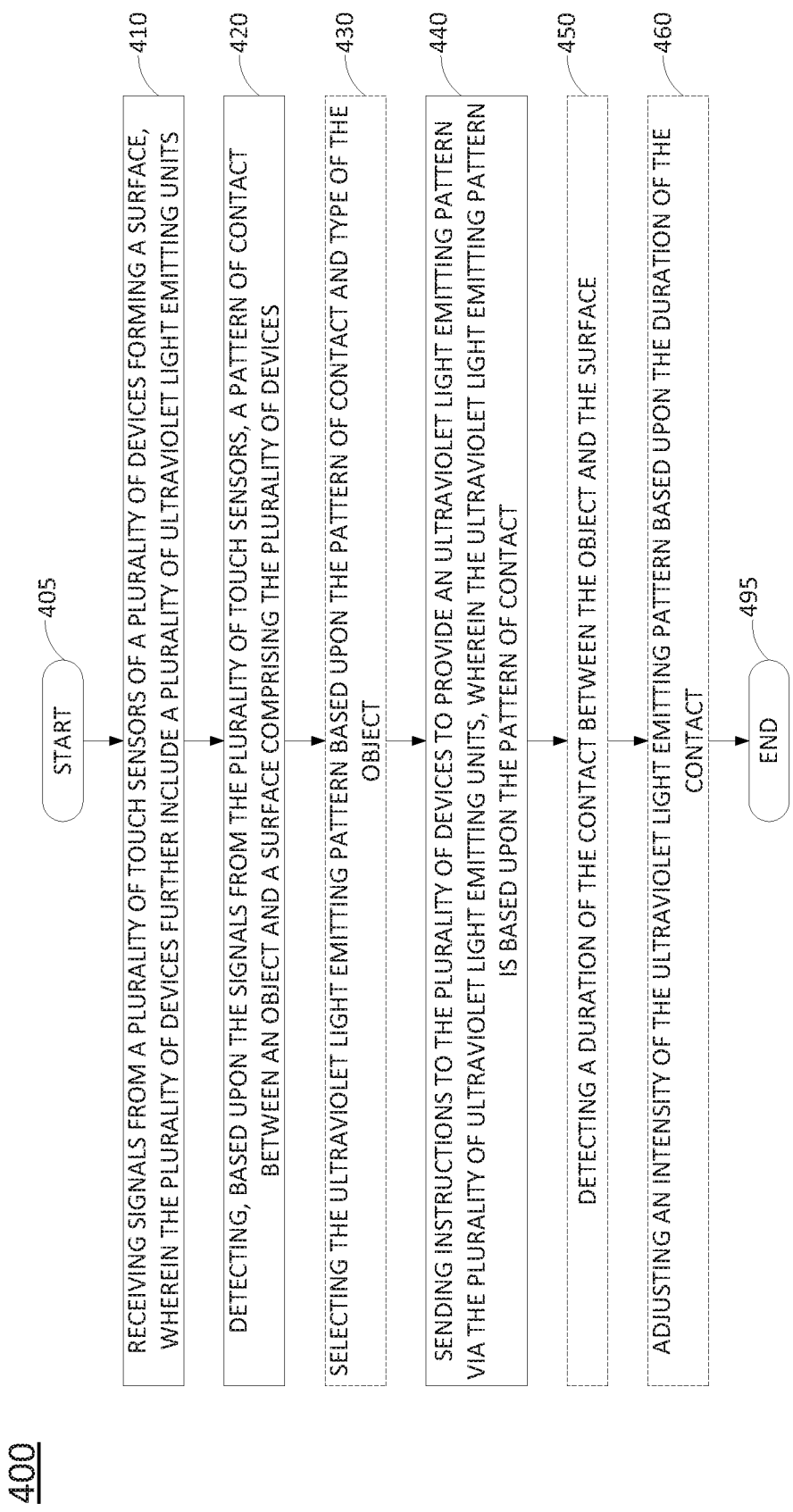
FIG. 4 illustrates a flowchart of an additional example method for sterilizing a surface and an object in contact with the surface, according to one embodiment of the present disclosure.

FIG. 4 illustrates a flowchart of an additional example method 400 for sterilizing a surface and an object in contact with the surface. In one example, the method 400 is performed by a controller, such as controller 290 of FIG. 2. In another example, the method 400 is performed by a device such as tile 100 of FIG. 1, or any of tiles 210-269 of FIG. 2. Alternatively, or in addition, the steps, functions, or operations of method 400 may be performed by a device or system 600, and/or processor 602 as described in connection with FIG. 6 below. For instance, the system 600 may represent a tile 100 of FIG. 1, a controller 290 or any of tiles 210-269 of FIG. 2. Similarly, in one example, the steps, functions, or operations of method 400 may be performed by a processing system comprising one or more computing devices collectively configured to perform various steps, functions, and/or operations of the method 400. For instance, multiple instances of the computing device or processing system 600 may collectively function as a processing system, e.g., multiple tiles, a controller and/or a controller in conjunction with one or more tiles, and so forth. For illustrative purposes, the method 400 is described in greater detail below in connection with an example performed by a processor, such as processor 602. The method begins in step 405 and proceeds to step 410.

At step 410, the processor receives signals from a plurality of touch sensors of a plurality of devices forming a surface. In other words, the devices, e.g., tiles, may include one or more patterns that define an interlocking with a plurality of other devices/tiles to form one or more surfaces. The surface may comprise, for example, a floor, an escalator, a travellator, a conveyor belt, and so forth. The plurality of devices further includes a plurality of UV light sources. In one example, the signals may indicate respective tactile states of the plurality of touch sensors. In another example, the signals may indicate only touch sensors of devices which have been or are being contacted, where it is implicit that touch sensors of other devices are not being contacted and therefore do not send signals. In one example the signals from the plurality of touch sensors may also indicate a pressure or amount of force of a contact. The signals may be received via wired or wireless communication. In addition, the processor along with the devices forming the surface may comprise an ad hoc or mesh network for sending and receiving signals indicating tactile states, for receiving instructions for activating UV light sources, and so on.

At step 420, the processor detects, based upon the signals from the plurality of touch sensors, a pattern of contact between an object and the surface comprising the plurality of devices. In one example, the processor may determine which devices forming the surface are being contacted and which are not. In one example, the processor may further determine a type of object, a size of the object (e.g., an adult or a child), a small or large animal, a large piece of furniture or a small piece of furniture, a large or small box, and so forth. In one example, the processor may perform pattern matching to match a pattern of contact of an object with a surface to a library of known patterns. In one example, the pattern of contact may also comprise successive contacts of an object with different portions of the surface, such as footprints of a person walking across a room, for instance.

At optional step 430, the processor may select a UV light emitting pattern based upon the pattern of contact and the type of the object. For instance, the UV light emitting pattern may comprise an application of a lesser intensity UV light at UV light sources of devices at an edge of the pattern of contact as compared to an intensity or intensities of UV light at UV light sources of devices within an interior of the pattern of contact. In one example, the plurality of UV light sources includes UV emitters in a plurality of UV wavelength bands. In such an example, the UV light emitting pattern may comprise an application of only ultraviolet C-band emitters at UV light sources of devices at an edge of the pattern of contact. In still another example, the UV light emitting pattern may comprise an activation of the UV light sources of devices in an interior of the pattern of contact, with activation of the UV light sources of devices at an edge of the pattern of contact being suppressed. For example, a device may be configured to activate a UV light source in one or more UV bands in response to the detection of a contact of an object with the device via a touch sensor of the device. However, an instruction received by the device within a certain period of time directing the device to not activate the UV light source may override this default configuration.

In general, some implementations may call for devices on the edges of a pattern of contact to use a lesser intensity of UV light or to not activate in order to provide a guard band and prevent UV light from spilling over. In another example, extra UV activation may be provided in devices that are not contacted, but which are near/adjacent to the devices that are contacted. Therefore, UV activation may be expanded beyond the devices that are actually contacted by a footstep or other objects. In one example, a lesser intensity of UV light may be used on devices outside of the actual pattern of contact (e.g., to avoid skin exposure). In another example, a higher intensity may be used, to give a better chance of decontamination on the irregularly shaped surfaces of a person's pants, shoelaces, or other hanging clothing. In addition, the UV light emitting pattern that is selected may vary depending upon the type of object (e.g., live versus inanimate, human versus non-human, etc.), the size of the object, and so on.

At step 440, the processor sends instructions to the plurality of devices to provide a UV light emitting pattern via the plurality of UV light sources, where the UV light emitting pattern is based upon the pattern of contact. For instance, the UV light emitting pattern may be selected at optional step 430, as described above. The instructions may be sent to the plurality of devices via wired and/or wireless communication depending upon the particular system in use and the capabilities and configurations of the processor and the devices in communication with the processor. In this regard, the devices may also include processors, microcontrollers, or the like to receive instructions and to activate UV light sources in accordance with the instructions received.

At optional step 450, the processor may detect a duration of the contact between the object and the surface. For instance, successive signals of the plurality of touch sensors over a period of time may indicate to the processor a continuing contact between an object and the surface.

At optional step 460, the processor may adjust an intensity of the UV light emitting pattern based upon the duration of the contact. For instance, in one example, the intensity of the UV light emitting pattern (e.g., the intensity or intensities of UV light emitted from the plurality of UV light sources) may be reduced for longer contacts. In another example, the intensity of the UV light emitting pattern may initially be increased for longer contacts, but may later be reduced if the passage of time corresponds to the portion of the object contacting the surface being fully or sufficiently sterilized. Following step 440 or optional 460, the method 400 proceeds to step 495 where the method ends.

Figure 5:
FIG. 5 illustrates a flowchart of another example method for sterilizing a surface and an object in contact with the surface, according to one embodiment of the present disclosure.

FIG. 5 illustrates a flowchart of an example method 500 for sterilizing a surface and an object in contact with the surface. In one embodiment, the method 500 is performed by a device such as tile 100 of FIG. 1, or any of tiles 210-269 of FIG. 2. Alternatively, or in addition, the steps, functions, or operations of method 500 may be performed by a device or system 600, and/or processor 602 as described in connection with FIG. 6 below. For instance, the system 600 may represent a tile 100 of FIG. 1, or any of tiles 210-269 of FIG. 2. For illustrative purposes, the method 500 is described in greater detail below in connection with an example performed by a processor, such as processor 602. The method begins in step 505 and proceeds to step 510.

At step 510, the processor detects, via the touch sensor, a tactile state of a device of the processor. For instance, the processor may be embedded in or otherwise comprise a component of a tile such as illustrated in FIGS. 1 and 2. In one example, step 510 may comprise the same or similar operations as described above in connection with step 310 of the method 300. In addition, the device and one or more additional devices may be deployed in a surface, in accordance with the present disclosure.

At step 520, the processor reports the tactile state of the device to a controller. In one example, the controller may be an external controller, e.g., external to a surface or grid formed of a number of tiles, in accordance with the present disclosure. In another example, the controller may be another device/tile forming the surface which is in communication with the device of the processor. In one example, the tactile state may be reported as being either a "contact" state or a "non-contact" state. In one example, the tactile state that is reported may further indicate a pressure or amount of force of a contact. In one example, the reporting of step 520 may be via wired or wireless communication depending upon the particular configuration of the system and the capabilities of the processor and the controller.

At step 530, the processor receives an instruction from the controller, the instruction for operating a UV light source of the device. In one example, the instruction may be sent as described above in connection with step 440 of the method 400.

At step 540, the processor implements an action associated with the UV light source in response to the instruction. For instance, the processor may activate the UV light source, may activate the UV light source with a particular intensity, a particular rate of increase or decay of the intensity, a particular band or bands of UV light, a particular duration of application, and so forth, depending upon the contents of the instruction. In another example, the processor may suppress an activation of the UV light source. For instance, the processor may be configured to activate the UV light source in one or more UV bands in response to the detection of a contact of an object with the device via a touch sensor of the device. However, an instruction received from the controller within a certain period of time directing the processor to not activate the UV light source may override this default configuration. Following step 540, the method 500 proceeds to step 595 where the method ends.

It should be noted that any of the methods 300, 400, and 500 may be expanded to include additional steps or may be modified to include additional operations with respect to the steps outlined above. For example, the respective methods 300, 400, and 500 may be repeated through various cycles of touch sensor signals and applications of UV light emission patterns. For instance, in one example, the method 400 may comprise tracking a person's footprints as the person walks across a surface and successively reducing the intensity and/or duration of application of UV light for each successive footstep. In such an example, the activation of UV light may also be suppressed after a certain number of footsteps, e.g., after it is assumed that the soles of the user's shoes or bare feet have been fully or sufficiently sterilized. Accordingly, in one example, the pattern of contact may be determined at step 420 to comprise multiple contacts with the surface, and the UV light emitting pattern selected at optional step 430 may comprise an application of a diminishing intensity or a diminishing duration of UV light for each successive contact of the multiple contacts. In addition, various types of device and surfaces other than those specifically mentioned may be the subject of the respective methods 300-500.

In addition, although not specifically specified, one or more steps, functions or operations of the respective methods 300-500 may include a storing, displaying and/or outputting step as required for a particular application. In other words, any data, records, fields, and/or intermediate results discussed in the method can be stored, displayed and/or outputted either on the device executing the method or to another device, as required for a particular application. Furthermore, steps, blocks, functions or operations in any of FIGS. 3-5 that recite a determining operation or involve a decision do not necessarily require that both branches of the determining operation be practiced. In other words, one of the branches of the determining operation can be deemed as an optional step. Furthermore, steps, blocks, functions or operations of the above described method(s) can be combined, separated, and/or performed in a different order from that described above, without departing from the example examples of the present disclosure.

FIG. 6 depicts a high-level block diagram of a computing device or processing system specifically programmed to perform the functions described herein. As depicted in FIG. 6, the processing system 600 comprises one or more hardware processor elements 602 (e.g., a central processing unit (CPU), a microprocessor, or a multi-core processor), a memory 604 (e.g., random access memory (RAM) and/or read only memory (ROM)), a module 605 for sterilizing a surface and an object in contact with the surface, and various input/output devices 306 (e.g., storage devices, including but not limited to, a tape drive, a floppy drive, a hard disk drive or a compact disk drive, a receiver, a transmitter, a speaker, a display, a speech synthesizer, an output port, an input port and a user input device (such as a keyboard, a keypad, a mouse, a microphone and the like)). In accordance with the present disclosure input/output devices 606 may also include touch sensors, UV light sources, e.g., UV LEDs, transceivers, power units, and so forth. Although only one processor element is shown, it should be noted that the computing device may employ a plurality of processor elements. Furthermore, although only one computing device is shown in the figure, if the method 300, method 400, or method 500 as discussed above is implemented in a distributed or parallel manner for a particular illustrative example, i.e., the steps of the above method 300, method 400, or method 500, or the entire method 300, method 400, or method 500 is implemented across multiple or parallel computing devices, e.g., a processing system, then the computing device of this figure is intended to represent each of those multiple computing devices.

Furthermore, one or more hardware processors can be utilized in supporting a virtualized or shared computing environment. The virtualized computing environment may support one or more virtual machines representing computers, servers, or other computing devices. In such virtualized virtual machines, hardware components such as hardware processors and computer-readable storage devices may be virtualized or logically represented. The hardware processor 602 can also be configured or programmed to cause other devices to perform one or more operations as discussed above. In other words, the hardware processor 602 may serve the function of a central controller directing other devices to perform the one or more operations as discussed above.

It should be noted that the present disclosure can be implemented in software and/or in a combination of software and hardware, e.g., using application specific integrated circuits (ASIC), a programmable gate array (PGA) including a Field PGA, or a state machine deployed on a hardware device, a computing device or any other hardware equivalents, e.g., computer readable instructions pertaining to the method discussed above can be used to configure a hardware processor to perform the steps, functions and/or operations of the above disclosed method 300, method 400, or method 500. In one example, instructions and data for the present module or process 605 for sterilizing a surface and an object in contact with the surface (e.g., a software program comprising computer-executable instructions) can be loaded into memory 604 and executed by hardware processor element 602 to implement the steps, functions or operations as discussed above in connection with the illustrative method 300, method 400, and/or method 500. Furthermore, when a hardware processor executes instructions to perform "operations," this could include the hardware processor performing the operations directly and/or facilitating, directing, or cooperating with another hardware device or component (e.g., a co-processor and the like) to perform the operations.

The processor executing the computer readable or software instructions relating to the above described method can be perceived as a programmed processor or a specialized processor. As such, the present module 605 for sterilizing a surface and an object in contact with the surface (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. Furthermore, a "tangible" computer-readable storage device or medium comprises a physical device, a hardware device, or a device that is discernible by the touch. More specifically, the computer-readable storage device may comprise any physical devices that provide the ability to store information such as data and/or instructions to be accessed by a processor or a computing device such as a computer or an application server.

While various examples have been described above, it should be understood that they have been presented by way of illustration only, and not a limitation. Thus, the breadth and scope of any aspect of the present disclosure should not be limited by any of the above-described examples, but should be defined only in accordance with the following claims and their equivalents.

What is claimed is:

1. A device comprising a plurality of tiles, wherein each tile of the plurality of tiles comprises:
   an ultraviolet light source comprising ultraviolet emitters in a plurality of ultraviolet wavelength bands;
   a touch sensor;
   a processor; and
   a computer-readable medium storing instructions which, when executed by the processor, cause the processor to perform operations, the operations comprising:
      detecting, via the touch sensor of a respective tile, a tactile state of the respective tile;
      detecting a tactile state of at least one additional tile of the plurality of tiles;
      determining, based upon the tactile state of the respective tile and the tactile state of the at least one additional tile, that the respective tile is on an interior of a pattern of contact between an object and a surface comprising the respective tile and the at least one additional tile; and activating the ultraviolet light source in response to the determining that the respective tile is on the interior of the pattern of contact, wherein the activating comprises applying at least one ultraviolet wavelength band of the plurality of ultraviolet wavelength bands based on a type of the object.

2. The device of claim 1, wherein the tactile state of the respective tile is a contact state and the tactile state of the at least one additional tile is a contact state.

3. The device of claim 2, wherein the activating comprises increasing an intensity of the ultraviolet light source.

4. The device of claim 2, wherein the activating comprises activating only an ultraviolet C-band portion of the ultraviolet light source when the object is bare skin.

5. The device of claim 1, wherein the tactile state of the respective tile is a contact state and the tactile state of the at least one additional tile is a non-contact state.

6. The device of claim 5, further comprising:
suppressing an activation of the ultraviolet light source at least in a region of the at least one additional tile.

7. The device of claim 1, further comprising:
a power source, wherein the power source comprises at least one of:
a piezoelectric transducer;
a fluid motion capture unit; or
a solar cell.

8. The device of claim 1, wherein the respective tile includes a pattern that defines an interlocking with a plurality of additional tiles of the plurality of tiles including the at least one additional tile to form the surface.

9. The device of claim 1, further comprising:
a transceiver, wherein the detecting the tactile state of the at least one additional tile comprises receiving data regarding the tactile state of the at least one additional tile via the transceiver.

10. The device of claim 1, wherein the surface comprises:
a floor;
an escalator;
a travellator; or
a conveyor belt.

11. The device of claim 1, wherein the activating comprises applying a first ultraviolet wavelength band of the plurality of ultraviolet wavelength bands near a first region of the object and applying a second ultraviolet wavelength band of the plurality of ultraviolet wavelength bands near a second region of the object.

12. The device of claim 1, further comprising:
identifying the object by matching the pattern of contact to a pattern in a library of known patterns.

13. A method comprising:
detecting, by a processor of a first tile of a device comprising a plurality of tiles, a tactile state of the first tile via a touch sensor;

detecting, by the processor, a tactile state of at least one additional tile of the plurality of tiles;

determining, by the processor, based upon the tactile state of the first tile and the tactile state of the at least one additional tile, that the first tile is on an interior of a pattern of contact between an object and a surface comprising the first tile and the at least one additional tile; and activating, by the processor, an ultraviolet light source in response to the determining that the first the is on the interior of the pattern of contact, wherein the activating comprises applying at least one ultraviolet wavelength band of a plurality of ultraviolet wavelength bands based on a type of the object.

14. The method of claim 13, wherein the tactile state of the first tile is a contact state and the tactile state of the at least one additional tile is a contact state.

15. The method of claim 14, wherein the activating comprises increasing an intensity of the ultraviolet light source.

16. The method of claim 14, wherein the activating comprises activating only an ultraviolet C-band portion of the ultraviolet light source when the object is bare skin.

17. The method of claim 13, wherein the tactile state of the first tile is a contact state and the tactile state of the at least one additional tile is a non-contact state.

18. The method of claim 17, further comprising:
suppressing an activation of the ultraviolet light source at least in a region of the at least one additional tile.

19. The method of claim 13, wherein the first tile includes a pattern that defines an interlocking with a plurality of additional tiles including the at least one additional tile to form the surface.

20. A non-transitory computer-readable storage medium storing instructions which, when executed by a processor, cause the processor to perform operations, the operations comprising:
detecting a tactile state of a first tile of a device comprising a plurality of tiles via a touch sensor;

detecting a tactile state of at least one additional tile of the plurality of tiles;

determining based upon the tactile state of the first tile and the tactile state of the at least one additional tile, that the first tile is on an interior of a pattern of contact between an object and a surface comprising the first tile and the at least one additional tile; and activating an ultraviolet light source in response to the determining that the first tile is on the interior of the pattern of contact, wherein the activating comprises applying at least one ultraviolet wavelength band of a plurality of ultraviolet wavelength bands based on a type of the object.

* * * * *